United States Patent [19]

Lorenz

[11] Patent Number: 4,492,796
[45] Date of Patent: Jan. 8, 1985

[54] ISOINDOLENINE DERIVATIVES, PROCESSES FOR THEIR PREPARATION AND THEIR USE AS INTERMEDIATE PRODUCTS FOR THE PREPARATION OF DYESTUFFS

[75] Inventor: Manfred Lorenz, Cologne, Fed. Rep. of Germany

[73] Assignee: Bayer Aktiengesellschaft, Leverkusen, Fed. Rep. of Germany

[21] Appl. No.: 268,963

[22] Filed: Jun. 1, 1981

[30] Foreign Application Priority Data

Jun. 19, 1980 [DE] Fed. Rep. of Germany ....... 3022839

[51] Int. Cl.³ .......................................... C07D 209/44
[52] U.S. Cl. .................................. 548/471; 548/482; 544/300; 544/301
[58] Field of Search ............... 260/326.1; 544/300, 544/301; 548/471, 482

[56] References Cited

U.S. PATENT DOCUMENTS

| | | | |
|---|---|---|---|
| 3,484,454 | 12/1969 | Pugini et al. | 260/326.1 |
| 3,923,806 | 12/1975 | Bock et al. | 544/300 |
| 3,987,045 | 10/1976 | Bock et al. | 544/300 |
| 4,111,947 | 9/1978 | L'Eplattenier et al. | 546/7 |
| 4,130,560 | 12/1978 | Habermeier | 544/321 |
| 4,166,179 | 8/1979 | Lotsch | 544/296 |

FOREIGN PATENT DOCUMENTS

| | | | |
|---|---|---|---|
| 576722 | 5/1959 | Canada | 548/471 |
| 1670748 | 5/1973 | Fed. Rep. of Germany | |
| 2628409 | 1/1979 | Fed. Rep. of Germany | 260/326.1 |
| 2,757,982 | 6/1979 | Fed. Rep. of Germany | 544/300 |
| 2,024,838 | 1/1980 | United Kingdom | 544/300 |

OTHER PUBLICATIONS

Angewandte Chemi, Isoindolenine als Zwischenprodukte der Phthalocyanin-Synthese, Dr. Berthold Bienert et al., 68, 133-150, (1956).
Journal of Organic Chemistry, Band 44, Nr 5, Mar. 2, 1979, Seiten, 1562, 1563-J. M. McCall et al: "Cyanoimine chemistry: New Routes to Pyrimidinones and (Carbonylamino)-Imino-Propanamides".
Chemische Berichte, Jahrgang 106, 1973, Seiten 956-961, W. Merkel et al., "Uber die Struktur des 4-(-Cyanamino)".

Primary Examiner—Donald G. Daus
Assistant Examiner—G. Hendricks
Attorney, Agent, or Firm—Sprung, Horn, Kramer & Woods

[57] ABSTRACT

Compounds which, in one of their tautomeric structures, correspond to the formula

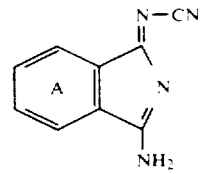

in which the ring A can carry 1, 2, 3 or 4 identical or different substituents, processes for their preparation and their use as intermediate products for the preparation of dyestuffs.

2 Claims, No Drawings

ISOINDOLENINE DERIVATIVES, PROCESSES FOR THEIR PREPARATION AND THEIR USE AS INTERMEDIATE PRODUCTS FOR THE PREPARATION OF DYESTUFFS

The invention relates to compounds which, in one of their tautomeric structures, correspond to the formula

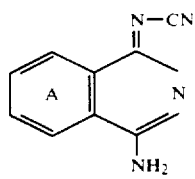

in which the ring A can carry 1, 2, 3 or 4 identical or different substituents.

The ring A can be substituted, for example, by halogen, nitro, alkyl, alkoxy, alkylsulphonyl, arylsulphonyl, phenyl, cyano, amino and/or acylamino.

Preferred substituents are chlorine, bromine, nitro, $C_1$-$C_6$-alkyl, in particular methyl and ethyl, $C_1$-$C_6$-alkoxy, in particular methoxy and ethoxy, $C_1$-$C_6$-alkylsulphonyl, in particular methylsulphonyl, phenylsulphonyl, phenyl, cyano, amino, mono-$C_1$-$C_4$-alkylamino, in particular acetylamino, and di-$C_1$-$C_4$-alkylamino.

The substituted ring A preferably carries one substituent.

The most important compound corresponds, in one of its tautomeric structures, to the formula

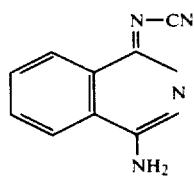

The new compounds of the formula I can be prepared in various ways. A preferred synthesis route consists in reacting an optionally substituted phthalic acid dinitrile with cyanamide in the presence of a basic compound, if appropriate in a suitable solvent or diluent.

Phthalic acid dinitriles which are suitable as starting materials for a synthesis of this type are, for example: phthalic acid dinitrile, 3-nitrophthalic acid dinitrile, 4-nitrophthalic acid dinitrile, 4-chlorophthalic acid dinitrile, 4,5-dichlorophthalic acid dinitrile, 4-aminophthalic acid dinitrile, 4-acetylaminophthalic acid dinitrile, 4-phenylphthalic acid dinitrile and 4-phenylsulphonylphthalic acid dinitrile.

Basic compounds which can be employed are, for example, alkali metal alcoholates or alkaline earth metal alcoholates, preferably of lower alcohols, such as sodium methylate or ethylate, and also alkali metal hydroxides and alkaline earth metal hydroxides, such as sodium hydroxide, potassium hydroxide and lithium hydroxide, sodium amide and, above all, the alkali metal salts of cyanamide and the alkali metal salts of compounds of the formula I.

Suitable solvents and diluents are, preferably, lower alcohols, such as methanol, ethanol, propanol and i-propanol, and glycols and glycol derivatives, such as ethylene glycol, glycol monomethyl ether, glycol monoethyl ether, diethylene glycol monomethyl ether and diethylene glycol monoethyl ether.

Other solvents and diluents which are possible are: cyclic or open-chain ethers, such as tetrahydrofuran, dioxane, ethylene glycol dimethyl ether, diethylene glycol dimethyl ether, diethylene glycol diethyl ether and oligo- and poly-glycols. Formamide, methylformamide, dimethylformamide, dimethylacetamide, N-methylpyrrolidone and dimethylsulphoxide are also particularly suitable solvents.

In addition, many of the customary organic solvents can be employed, as long as they have a sufficient dissolving power for the substances to be reacted and do not lead to undesired side reactions.

If this solubility is in itself too low, the solvents can also be employed as additional solvents. Such customary organic solvents are, for example, benzene, toluene, xylene, chlorobenzene, dichlorobenzene, nitrobenzene, pyridine, quinoline and chlorotoluene.

In detail, the reaction is carried out by a procedure in which the components are mixed in any desired sequence, during which it may be appropriate, depending on the circumstances, such as the nature and concentration of the compounds employed, to remove the heat of reaction by cooling or to accelerate the reaction by heating. In general, the reaction is carried out and the components are brought together in a temperature range such that excessive cooling or warming is avoided. Such a favourable temperature range is, for example, between about 0° and about 100° C., but, if necessary, the reaction can also be carried out at lower and higher temperatures.

The basic compounds added serve as catalysts and accordingly do not have to be employed in stoichiometric amounts; however, it is of course unprofitable to use very large amounts of catalysts, but on the other hand the reaction proceeds at an unprofitably slow rate if the amounts of catalyst are too small. Favourable amounts of catalyst are between about 0.1 and 2-3 mols, per mol of phthalic acid dinitrile.

It is expedient to add the cyanamide in equivalent amounts or in a small excess, but larger and smaller amounts are, of course, likewise possible. The compounds of the formula I are obtained in the reaction completely or partly as salts, and they can be isolated as such in the customary manner, for example by evaporation, precipitation, extraction or, if appropriate, filtration.

If water-miscible solvents are used, it may be advantageous to dilute the mixture with water when the reaction has ended and to precipitate the product by neutralisation or acidification. In many cases, isolation can be dispensed with entirely and the reaction mixtures can be further reacted directly.

Particular circumstances may result if asymmetrically substituted phthalodinitriles are employed. In this case, two isomeric compounds can be formed, depending on which nitrile group attacks the cyanamide. Mixtures of the two isomers of various composition, or only one of the isomers, can be formed, depending on the nature of the substituents. Which of the possible isomers is predominantly formed probably depends on the nature of the substituents, details of this formation not being known.

A second way of preparing compounds of the formula I consists in allowing compounds of the formula III or compounds of the formula IV to react with cyanamide.

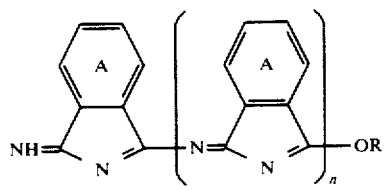

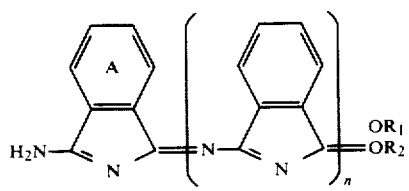

In the formulae III and IV, A has the abovementioned meanings, n designates 0 or an integer, preferably 1, 2, 3, 4 or 5, and R, $R_1$ and $R_2$ represent alkyl, preferably $C_1$–$C_6$-alkyl, which can be substituted, for example by —CN, or represent aralkyl, preferably benzyl or phenethyl, cycloalkyl, preferably cyclopentyl or cyclohexyl, aryl, preferably phenyl, or —$CH_2$—$CH_2$—O—$CH_2$—$CH_2$—$)_m$—OH radicals wherein m designates an integer from 0 to 40. $R_1$ and $R_2$, together with the two O atoms and the C atom of the isoindolenine system, can also form a 5-membered or 6-membered heterocyclic ring, which can be substituted, for example by 1 or 2 $C_1$–$C_4$-alkyl radicals, preferably methyl radicals.

Compounds of the formulae III and IV are obtained, for example, in the reaction of alcohols or glycols with phthalic acid dinitriles in the presence of basic compounds. They can thus be formed as an intermediate product in the reaction, described in the preceding paragraph, of phthalic acid dinitriles with cyanamide in alcoholic solvents. However, they can also be prepared in a special reaction step and thereby be reacted with cyanamide, with or without intermediate isolation, it being possible to apply the same conditions as in the direct reaction of phthalic acid dinitriles with cyanamide. Suitable compounds of the formula III are, for example, 3-ethoxy- or 3-isopropoxy-1-imino-isoindolenine; examples of compounds of the formula IV are 3,3-dimethoxy-1-imino-isoindolenine and 3,3-diethoxy-1-aminoisoindolenine. Finally, oligomeric or polymeric compounds of the possible formulae III and IV in which n>0 and which can be used in the same manner can be formed in the reaction of alcohols with phthalic acid dinitriles or with amino-imino-isoindolenine under suitable conditions (see, for example, Angew. Chemie 68, 133 (1956)).

Another way of preparing compounds of the formula I consists in reacting compounds of the formula

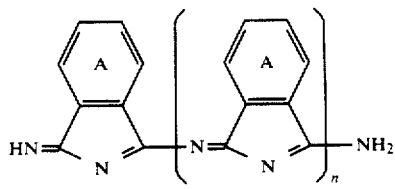

in which A and n have the abovementioned meanings, with cyanamide.

Compounds of the formula V are formed, for example, in the reaction of optionally substituted phthalic acid dinitriles with ammonia, 1-amino-3-iminoisoindolenine being formed in the simplest case (n=0).

The compounds of the formula V react with cyanamide under similar conditions to the phthalodinitriles themselves, up to one equivalent of ammonia being liberated. However, it is expedient to choose somewhat higher reaction temperatures when starting compounds of the formula V are used, in order to achieve a sufficient rate of reaction. Temperatures between 20° and 100° C. are suitable and adequate.

The substances of the formula I are compounds which crystallise well and which, in the IR spectrum, exhibit a pronounced nitrile band at 2,200 $cm^{-1}$.

The compounds of the formula I are particularly suitable as starting materials for the preparation of dyestuffs. Thus, for example, a new, advantageous way of preparing pigment dyestuffs consists in subjecting compounds of the formula I to a condensation reaction with barbituric acid or derivatives thereof of the formula

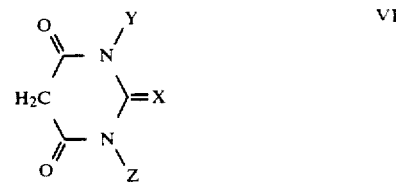

in a manner which is in itself known, to give dyestuffs of the formula VII

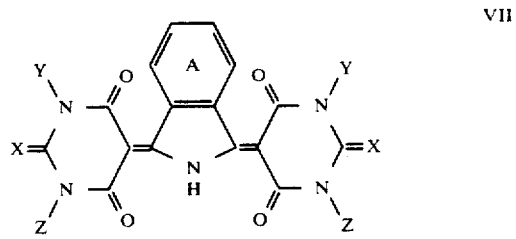

In the formulae VI and VII: X represents O, S, NH or N—CN and Y and Z represents H, $C_1$–$C_4$-alkyl, $C_5$–$C_6$-cycloalkyl or an optionally substituted phenyl radical. Phenyl radicals Y and Z can be substituted, for example by halogen, such as chlorine and bromine, $C_1$–$C_6$-alkyl, $C_1$–$C_6$-alkoxy, cyano, nitro, carbamoyl, sulphamoyl, acylamino, in particular ($C_1$–$C_6$-alkyl)-carbonylamino, or $C_1$–$C_6$-alkylsulphonyl. A has the abovementioned meanings.

Unsubstituted barbituric acid is the preferred reactant.

The condensation can be carried out by processes analogous to those in DE-OS (German Published Specification) No. 2,041,999, in organic solvents, if appropriate in the presence of organic or inorganic hydracids or ansolvoacids and/or of an acylating agent, in the temperature range from 80° to 200°.

A particularly advantageous process for the preparation of the pigment of the formula

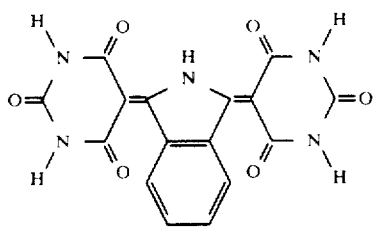

C.I. Pigment Yellow 139 consists in subjecting 1-amino-3-cyanimino-isoindolenine to a condensation reaction with barbituric acid in a molar ratio of 1:2, the condensation preferably being carried out in water in the pH range between 1 and 6 and, if appropriate, in the presence of surface-active compounds, at temperatures between 20° and 150° C. A procedure analogous to that in DE-OS (German Published Specification) No. 2,628,409 in which the condensation is carried out in water in the presence of mineral acids, aliphatic or aromatic carboxylic acids, aliphatic or aromatic sulphonic acids or mixtures of the acids mentioned, have proved particularly suitable.

By "parts" in the following examples there are understood parts by weight. These relate to parts by volume as g to ml.

The temperature data are in °C.

EXAMPLE 1

33.6 parts of monosodium cyanamide are stirred with 150 parts by volume of methanol. 64 parts of phthalic acid dinitrile are introduced at 30°–35° in the course of about 2–3 hours and the mixture is stirred overnight at room temperature. The reaction mixture is diluted with 300 parts by volume of ice-water and the solution is neutralised by dropwise addition of hydrochloric acid or acetic acid. A precipitate is formed, which is filtered off after 15 minutes, washed with water and dried at 60° in vacuo.

86 parts of a colourless, crystalline substance which has a melting point of 247°–250° and on analysis shows an empirical formula of $C_9H_6N_4 \cdot 1/2\ H_2O$ are obtained.

Analysis: calculated: C 60.3, H 3.9, N 31.3: found: C 60.2, H 4.1, N 31.2.

A comparable result is achieved if the methanol in Example 1 is replaced by glycol or methylglycol.

EXAMPLE 2

91 parts of disodium cyanamide are sprinkled into 800 parts by volume of methanol, during which the temperature is kept at 30°–35° by cooling. A total of 128 parts of phthalic acid dinitrile are then introduced in small portions in the course of about 1 hour in a manner such that the temperature does not exceed 60°, and the mixture is subsequently stirred for a further hour. The reaction mixture is then poured into 1,000 parts by volume of ice-water and is clarified and the filtrate is neutralised by dropwise addition of 210 parts by volume of 10N hydrochloric acid. A precipitate is obtained which is isolated and dried, as described in Example 1. The yield is 160 parts.

The product has the same properties as described in Example 1.

Instead of methanol, it is also possible to employ ethanol in Example 2 with comparable results.

EXAMPLE 3

64 parts of phthalic acid dinitrile and 200 parts by volume of methanol are stirred, and 46 parts of 30% strength sodium methylate solution are added. The mixture is heated to 55°–60° for 30 minutes. A dark-coloured solution of monomeric and oligomeric methoxyamino-isoindolenines of unknown composition is obtained. 21.5 parts of cyanamide are sprinkled into this mixture in the course of about 30 minutes and the mixture is stirred for a further hour at 60°. The resulting solution is introduced into 1,000 parts by volume of water and neutralised with 16 parts by volume of acetic acid. If the mixture is worked up as described in Example 1, 77.8 parts of 1-amino-3-cyanimino-isoindolenine are obtained.

EXAMPLE 4

If the procedure followed is as described in Example 3, but only 23 parts of sodium methylate solution are used, 1-amino-3-cyanimino-isoindolenine is obtained in the same yield as in Example 3.

EXAMPLE 5

128 parts of phthalic acid dinitrile are introduced into a solution of 12.5 parts of sodium in 1,000 parts by volume of ethanol at 25°, whilst cooling, and the mixture is subsequently stirred for 1.5 hours. 43 parts of cyanamide are added to this resulting suspension of 1-amino-3,3-diethoxy-isoindolenine and the mixture is then heated to 60° for 1 hour. Working up gives 170 parts of 1-amino-3-cyanimino-isoindolenine with the same properties as in Example 1.

EXAMPLE 6

73 parts of 1-amino-3-imino-isoindolenine are mixed with 500 parts by volume of methanol, and 33.6 parts of monosodium cyanamide are added and the mixture is heated under reflux for 2 hours, during which ammonia escapes. The solution is poured into 1,000 parts by volume of ice-water and the amino-cyaniminoisoindolenine is isolated as in Example 1. A yield of 68 parts is obtained.

EXAMPLE 7

63.2 parts of monosodium cyanamide are stirred with 1,500 parts by volume of methanol, and 163 parts of 4-chloro-phthalic acid dinitrile are introduced in the course of about 1 hour. The mixture is stirred overnight at room temperature and then diluted with 1,000 parts by volume of water, acidified with 100 parts by volume of acetic acid and subsequently stirred for 2 hours.

The precipitate which forms is filtered off and washed with methanol and water. 163 parts of 4- or 5-chloro-1-amino-3-cyaniminoisoindolenine with a melting point of 253°–256° C. are obtained. In the thin layer chromatogram, the substance is essentially a single compound.

Analysis: calculated: C 52.8, H 2.5, N 27.4: found: C 52.5, H 2.6, N 26.9.

EXAMPLE 8

If the procedure followed is as in Example 7, but 173 parts of 4-nitro-phthalic acid dinitrile are employed instead of the chlorophthalic acid dinitrile, 204 parts of 4- or 5-nitro-amino-3-cyanimino-isoindolenine are obtained. Melting point: 244°–251° C.

Analysis: calculated: C 50.2, H 2.3, N 32.6: found: C 49.9, H 2.6, N 32.2.

EXAMPLE 9

300 parts by volume of methanol and 37 parts of 4-acetylaminophthalic acid dinitrile are stirred, 13.5 parts of monosodium cyanamide are sprinkled in and the mixture is stirred overnight at room temperature and heated for a further hour under reflux. THe mixture is then neutralised, whilst still at the boiling point, by dropwise addition of 12 parts by volume of acetic acid. 300 parts by volume of ice-water are added to the suspension and the product is filtered off and washed with water. 39.5 parts of 4- or 5-acetylamino-1-amino-cyaniminoisoindolenine are obtained. The substance has no definite melting point.

EXAMPLE 10

27.2 parts of barbituric acid, 500 parts by volume of water and 7.7 parts by volume of formic acid are stirred and 17.9 parts of 1-amino-3-cyaniminobarbituric acid, prepared according to Example 1, are sprinkled in. The batch is stirred at 60° for 2 hours and under reflux for 4 hours. The precipitate is then filtered off and washed with 200 parts by volume of water of 80°. After drying the product at 70°, 35.5 parts of a yellow pigment of the formula are obtained.

Analysis: calculated: C 52.3, H 2.5, N 19.1: found: C 52.0, H 2.6, N 19.1.

EXAMPLE 11

If the procedure followed is as in Example 10, but 3 parts of an ethylene oxide/propylene oxide block polymer with a molecular weight of about 3,000 are additionally added to the reaction batch, 36.4 parts of the same pigment are obtained, but in a form which is more readily dispersible.

EXAMPLE 12

If the procedure followed is as described in Example 10, but an analogous amount of N,N'-dimethylbarbituric acid is employed instead of barbituric acid, 38.9 parts of a yellow dyestuff of the formula are isolated.

Analysis: calculated: C 56.7, H 4.0, N 16.5: found: C 56.6, H 3.9, N 16.4.

EXAMPLE 13

If a corresponding amount of 2-thiobarbituric acid is employed instead of barbituric acid in Example 10 and the procedure is otherwise as described in Example 10, 27.3 parts of the red dyestuff of the formula are obtained.

I claim:

1. A compound which, in one of its tautomeric structures, corresponds to the formula in which the ring A can be substituted by one substituent selected from the group consisting of chlorine, bromine, nitro, $C_1$-$C_6$-alkyl, $C_1$-$C_6$-alkoxy, $C_1$-$C_6$-alkylsulphonyl, phenylsulphonyl, phenyl, cyano, amino, mono-$C_1$-$C_4$-alkylamino, di-$C_1$-$C_4$-alkylamino and acetylamino.

2. Compound according to claim 1 which, in one of its tautomeric structures, corresponds to the formula